United States Patent
Lee et al.

(10) Patent No.: US 8,270,556 B2
(45) Date of Patent: Sep. 18, 2012

(54) APPARATUS FOR FORMING STRESS CORROSION CRACKS

(75) Inventors: Bo Young Lee, Goyang (KR); Jae Seong Kim, Goyang (KR); Woong Ki Hwang, Seoul (KR)

(73) Assignee: Industry-University Cooperation Foundation Hankuk Aviation University, Gyeonggi-do (KR)

( * ) Notice: Subject to any disclaimer, the term of this patent is extended or adjusted under 35 U.S.C. 154(b) by 372 days.

(21) Appl. No.: 12/325,877

(22) Filed: Dec. 1, 2008

(65) Prior Publication Data
US 2010/0091930 A1    Apr. 15, 2010

(30) Foreign Application Priority Data
Oct. 9, 2008    (KR) .................. 10-2008-0098982

(51) Int. Cl.
*G21C 9/00*    (2006.01)
(52) U.S. Cl. .................. 376/305; 376/277; 73/808
(58) Field of Classification Search .................. 376/305, 376/277; 73/808
See application file for complete search history.

(56) References Cited

U.S. PATENT DOCUMENTS

| | | | | |
|---|---|---|---|---|
| 2,739,829 | A | * | 3/1956 | Cundiff et al. ............... 285/21.2 |
| 4,098,172 | A | * | 7/1978 | Wright et al. .................... 92/161 |
| 4,229,235 | A | * | 10/1980 | Matsuda et al. ............... 148/520 |
| 4,354,883 | A | * | 10/1982 | Terasaki ........................ 148/520 |
| 4,948,435 | A | * | 8/1990 | Butler et al. .................. 148/529 |
| 5,034,190 | A | * | 7/1991 | Economy et al. ............... 422/53 |
| 5,361,284 | A | * | 11/1994 | Baum et al. .................... 376/245 |
| 2007/0084303 | A1 | * | 4/2007 | Bussu ............................ 73/866 |
| 2007/0295099 | A1 | * | 12/2007 | Lee et al. ........................ 73/808 |

FOREIGN PATENT DOCUMENTS
WO    WO 2005/023478    3/2005
* cited by examiner

*Primary Examiner* — Ricardo Palabrica
(74) *Attorney, Agent, or Firm* — IPLA P.A.; James E. Bame

(57) ABSTRACT

An apparatus for forming stress corrosion cracks comprises a heating unit which includes a conductive member and a heating coil disposed adjacent to the conductive member to generate steam pressure in the tube specimen, an end holding unit, and a control unit for controlling the heating unit and the end holding unit. The stress corrosion cracks occurring in the equipment of nuclear power plants or apparatus industries during operation can be directly formed in a tube specimen using steam pressure under conditions similar to those of the actual environment of nuclear power plants, thus increasing accuracy for analysis of properties of stress corrosion cracks which are in actuality generated, thereby improving reliability of nuclear power plants or apparatus industries and effectively assuring nondestructive testing capability, resulting in very useful industrial applicability.

5 Claims, 8 Drawing Sheets

APPARATUS FOR FORMING STRESS CORROSION CRACKS

CROSS REFERENCE

This application claims foreign priority under Paris Convention and 35 U.S.C. §119 to Korean Patent Application No. 10-2008-0098982, filed Oct. 9, 2008 with the Korean Intellectual Property Office.

BACKGROUND OF THE INVENTION

1. Field of the Invention

The present invention relates to an apparatus for forming stress corrosion cracks which occur in base metal or welded parts (which are homogeneous or heterogeneous) used in equipment such as reactor heads, steam generators or the like of nuclear power plants, and, more particularly, to an apparatus for forming stress corrosion cracks, in which stress corrosion cracks occurring in the equipment of nuclear power plants or apparatus industries during operation can be directly formed in a piping material actually used in nuclear power plants under environmental conditions similar to those of the nuclear power plants, thus predicting a crack propagation rate, thereby reducing actual risks of nuclear power plants or apparatus industries and effectively assuring nondestructive testing capability.

2. Description of the Related Art

As is well known to those skilled in the art, there is a need to construct an experimental apparatus which operates under environmental conditions similar to those existing actual conditions which generate stress corrosion cracks in nuclear power plants. However, in the case of stress corrosion cracks occurring in a primary system, such as a steam generator, a pressure vessel of a reactor or the like, there is a dangerous probability of emitting radioactivity due to the lack of domestic simulation techniques.

Thus, in order to ensure the safety of nuclear power plants and the reliability of NDT technologies, it is very important to realize techniques for producing natural cracks similar to actual defects occurring in nuclear power plants during operation.

To this end, an experimental apparatus able to simulate actual conditions for generating stress corrosion cracks in nuclear power plant structures must be constructed. If so, the reliability and safety of nuclear power plants may be improved and techniques for precisely diagnosing defects in the power plants occurring during their operation may be advanced.

In this way, when techniques for simulating stress corrosion cracks in a piping material actually used in nuclear power plants and for precisely diagnosing defects are ensured, inspection methods during the operation of the power plants may be developed and also data for safety regulation and repair criteria of nuclear power plant structures may be obtained.

With the goal of forming stress corrosion cracks in a specimen, the following testing method is mainly illustrated.

Specifically, a specimen is produced in the form of a C-ring or a U-band and is then loaded into an autoclave, after which appropriate tensile or compressive stress is applied thereto. In such a state, corrosion environmental conditions are set, and high-temperature high-pressure conditions are applied, thus forming crack.

However, the conventional method of forming stress corrosion cracks is disadvantageous because the resulting cracks are obtained not using a piping material actually used for equipment of nuclear power plants or apparatus industries but using a simulation specimen, they are considerably different from actual cracks, thus making it impossible to effectively assure nondestructive testing capability.

SUMMARY OF THE INVENTION

Accordingly, the present invention has been made keeping in mind the above problems encountered in the related art, and the present invention provides an apparatus for forming stress corrosion cracks, in which not a conventional specimen prepared according to a standard method (ASTM and so on) using an autoclave but a piping material actually used for equipment of nuclear power plants or apparatus industries is directly heated, so that stress corrosion cracks can be directly formed under conditions similar to those observed in nuclear power plants or apparatus industries using steam pressure generated by corrosion conditions in the pipe through direct heating, thus predicting a crack propagation rate, thereby reducing actual risks of nuclear power plants or apparatus industries and effectively assuring nondestructive testing capability.

According to a preferred embodiment of the present invention, an apparatus for forming stress corrosion cracks comprises a heating unit, which includes a conductive member provided on an outer surface of one side of a tube specimen in a circumferential direction and a heating coil disposed adjacent to the conductive member to generate steam pressure in the tube specimen, an end holding unit for closing both open ends of the tube specimen so that the steam pressure generated in the tube specimen does not leak, and a control unit for controlling the heating unit and the end holding unit.

As a preferred feature of the present invention, the heating unit may comprise an induction heating coil for inducing heating by forming a magnetic field using high-frequency current or a direct heating coil having a heating wire which is heated using power.

As another preferred feature of the present invention, the end holding unit may comprise an upper plate and a lower plate for closing both ends of the tube specimen, and a tension bar including a hydraulic or pneumatic cylinder using hydraulic or pneumatic pressure as an operation pressure or an actuator rod using power to adjust a distance between the upper plate and the lower plate.

As a further preferred feature of the present invention, the control unit may comprise a steam temperature measuring sensor for measuring a temperature of the steam in the tube specimen, an etchant temperature measuring sensor for measuring a temperature of an etchant in the tube specimen, a pressure measuring sensor for measuring an inner pressure of the tube specimen, and a controller electrically connected to the pressure measuring sensor to receive detection signals and to selectively output control signals to the heating unit and the end holding unit based on the received detection signals.

As still a further preferred feature of the present invention, in order to ensure accuracy and safety in the use of the pressure measuring sensor, a cooling unit for lowering the temperature of the steam pressure in the tube specimen may be connected to the lower plate so that steam in the specimen is passed through the cooling unit having at least a predetermined length for phase transformation of steam into water to lower the temperature of the steam and may be simply provided in the form of a coil made of corrosion resistant material.

The features and advantages of the present invention will be more clearly understood from the following detailed description, taken in conjunction with the accompanying drawings. The terms and words used in the specification and claims must be regarded as having concepts selected by the inventor as the best method of illustrating the present invention, and must be interpreted as having meanings and concepts adapted to the scope and sprit of the present invention for understanding the technology of the present invention.

DESCRIPTION OF THE PREFERRED EMBODIMENT

Figure 1:
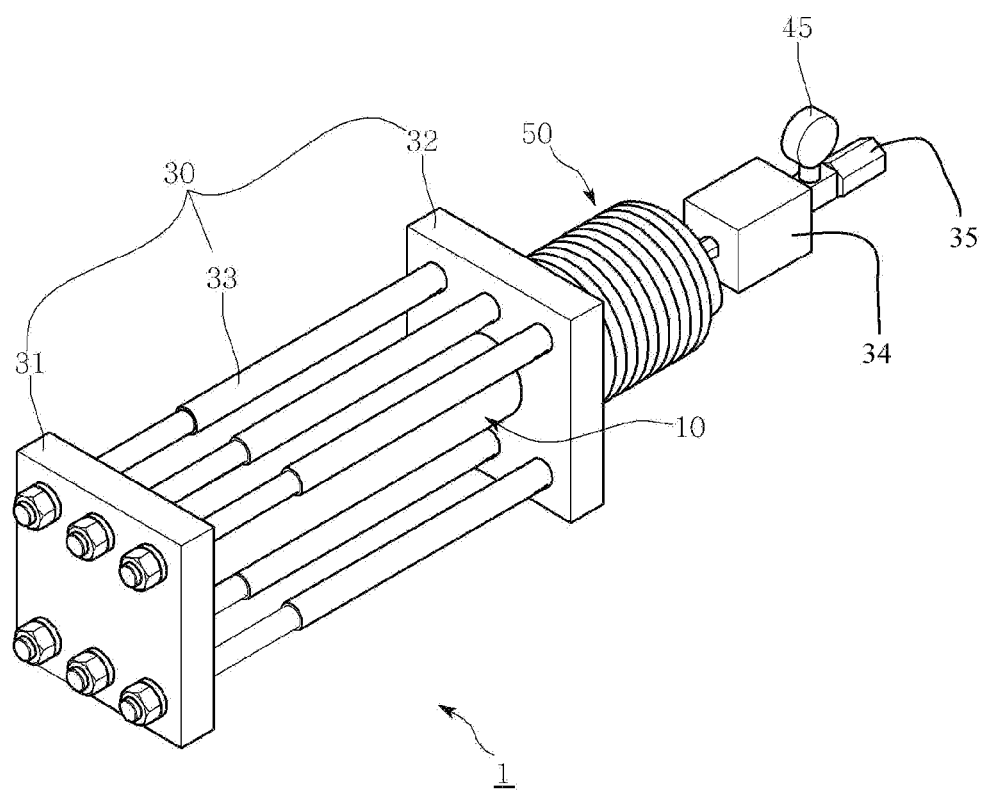
FIG. 1 shows a partial perspective view of a heating unit of an apparatus for forming stress corrosion cracks according to the present invention.

Hereinafter, a detailed description will be given of an apparatus for forming stress corrosion cracks according to a preferred embodiment of the present invention with reference to the appended drawings.

In the drawings, it is noted that the same reference numerals are used throughout the different drawings to designate the same or similar components. In the present invention, a detailed description of functions or structures known in the related art is omitted so as not to obscure the purpose of the present invention.

Figure 2:
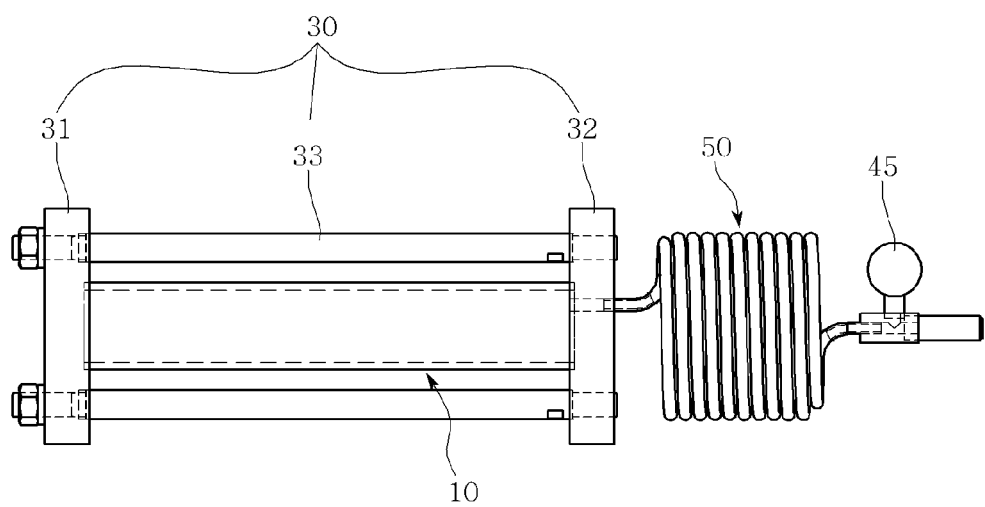
FIG. 2 shows main components of the apparatus for forming stress corrosion cracks according to the present invention.

FIG. 1 shows a partial perspective view of the heating unit of the apparatus for forming stress corrosion cracks according to the present invention, and FIG. 2 shows main components of the apparatus for forming stress corrosion cracks according to the present invention.

Figure 3:
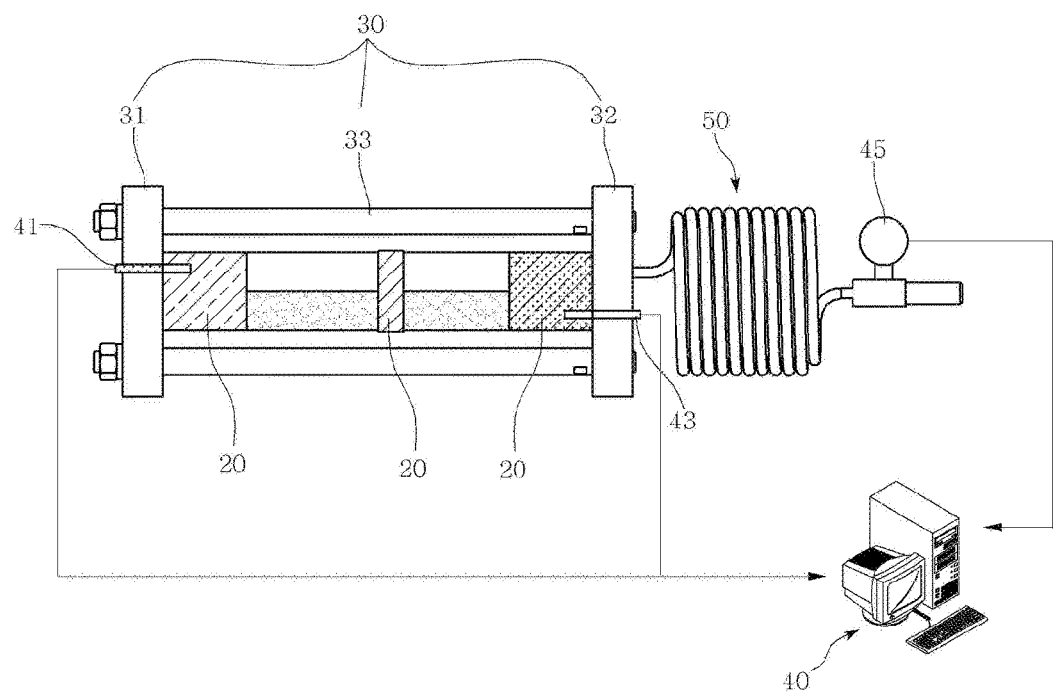
FIG. 3 schematically shows the operation of the apparatus for forming stress corrosion cracks according to the present invention.
Figure 4:
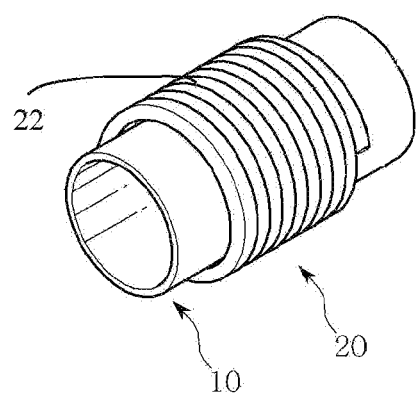
FIG. 4 schematically shows the heating unit according to the present invention.
Figure 5:
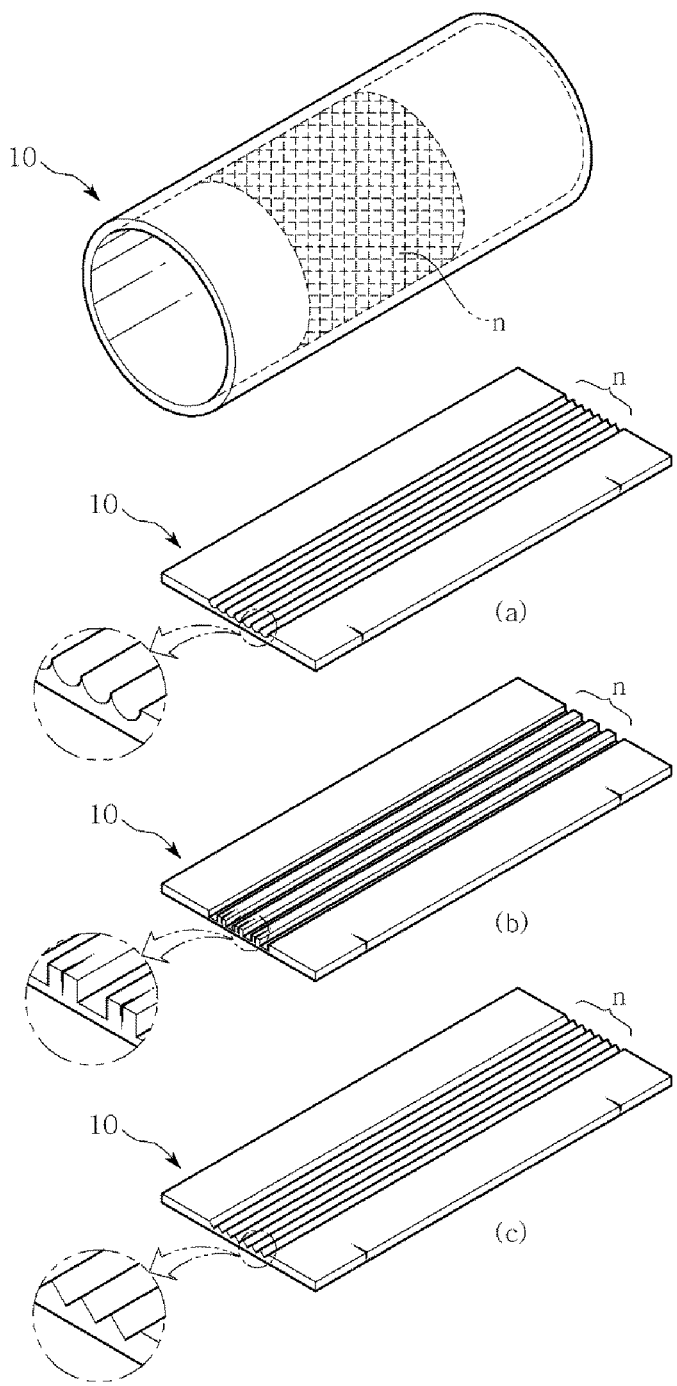
FIG. 5 shows the position and pattern of notches formed in a tube specimen according to the present invention.

Also, FIG. 3 schematically shows the operation of the apparatus for forming stress corrosion cracks according to the present invention, FIG. 4 schematically shows the heating unit according to the present invention, and FIG. 5 shows the position and pattern of notches formed in a tube specimen according to the present invention.

As shown in the drawings, the apparatus 1 for forming stress corrosion cracks according to the preferred embodiment of the present invention includes a heating unit 20 having a direct heating coil or an induction heating coil disposed adjacent to a specimen 10 having a tube shape (hereinafter referred to as a "tube specimen 10"), an end holding unit 30 for maintaining steam pressure generated due to heating, a cooling unit for decreasing steam pressure, and a measurement unit for measuring pressure. The end holding unit 30 comprises an upper plate 31 and a lower plate 32 for closing both ends of the tube specimen 10, and a tension bar 33 including a hydraulic or pneumatic cylinder 34 using hydraulic or pneumatic pressure as an operation pressure or an actuator rod 35 using power to adjust a distance between the upper plate 31 and the lower plate 32.

The heating unit 20 functions to apply predetermined heat to the outer surface of one side of the tube specimen 10 to set application environments of temperature and pressure required to form stress corrosion cracks of the tube specimen 10. Examples of the material for the tube specimen 10 include STS 304, STS 316, STS 321, STS 347, STS 308, STS 309, Inconel 600, Inconel 690, Inconel 800, Inconel X750, and Inconel 718, which are actually used as pipes of nuclear power plants or apparatus industries. Also, homogeneous or heterogeneous welded parts for use in nuclear power plants may be used.

The heating unit 20 is composed of a conductive member 21 made of magnetic material and attached to the outer surface of one side of the tube specimen 10 in a circumferential direction, and an induction coil or a direct heating coil spaced apart from the conductive member. The heating unit 20 comprises a direct heating coil 22 which is heated using power.

To the induction coil is connected an external high-frequency current supplier. When high-frequency current is applied to the induction coil from the high-frequency current supplier, a high-frequency magnetic field is formed in the induction coil, and thus the conductive member adjacent to the induction coil is heated by eddy current loss or hysteresis loss occurring due to the high-frequency magnetic field, thus heating the outer surface of one side of the tube specimen 10 to which the conductive member is attached to a predetermined temperature.

The heating process using the induction coil may be conducted through any technique known in the art, and a description thereof is omitted.

Alternatively, when alternating current of 220 V is applied to the heating coil, the outer surface of one side of the tube specimen 10 to which the coil is attached may be heated to a predetermined temperature. The heating process using the heating coil may be conducted through any technique known in the art.

On the inner surface of the tube specimen 10, a notch n enabling the formation of a stress corrosion crack at a desired position through mechanical or chemical processing such as lathe machining may be formed. The width of the notch n may be set to about 0.5~50 mm, and the notch n may be provided in various forms, for example, ∪, v, and ⌐, as illustrated in (a), (b) and (c) of FIG. 5. In this way, when the notch n is formed on a portion of the inner surface of the tube specimen 10, a position where a stress corrosion crack is generated may be easily controlled and a period of time required to form such a crack may be reduced, compared to when no notch is provided.

The end holding unit 30 functions to stably maintain the steam pressure generated in the tube specimen 10 by means of the heating unit 20. If the end holding unit 30 has a structural feature able to stably close both ends of the tube specimen 10 to stably maintain the steam pressure in the tube specimen 10, a member having various shapes may be applied.

In the present invention, as illustrated in the drawing, the end holding unit 30 preferably includes an upper plate 31 and a lower plate 32 respectively provided at both ends of the tube specimen 10 and a tension bar 33 for adjustably connecting the upper plate 31 and the lower plate 32.

The upper plate 31 and the lower plate 32 may be respectively connected to both ends of the tube specimen 10 using a mechanical process or a hydraulic or pneumatic tool, thereby firmly holding both ends of the tube specimen 10. Such a connection process may be performed through any technique known in the art.

The cooling unit 50 functions to lower the temperature of the steam pressure in the tube specimen 10. In order to ensure accuracy and safety in the use of a pressure measuring sensor, the cooling unit is connected to the lower plate 32 so that steam in the specimen is passed through the cooling unit having at least a predetermined length for phase transformation of steam into water to lower the temperature of the steam, and is simply provided in the form of a coil made of corrosion resistant material.

The control unit 40 functions to rapidly heat the tube specimen using the heating unit 20 through on/off control and to control the temperature of the steam generated by the increase in the temperature of the etchant in the heated tube specimen through PWM control before reaching desired pressure. When the control unit is used, the temperature of the steam may be controlled to about 10° C. or lower, thereby continuously maintaining the steam pressure of 170~180 bar.

Figure 6:
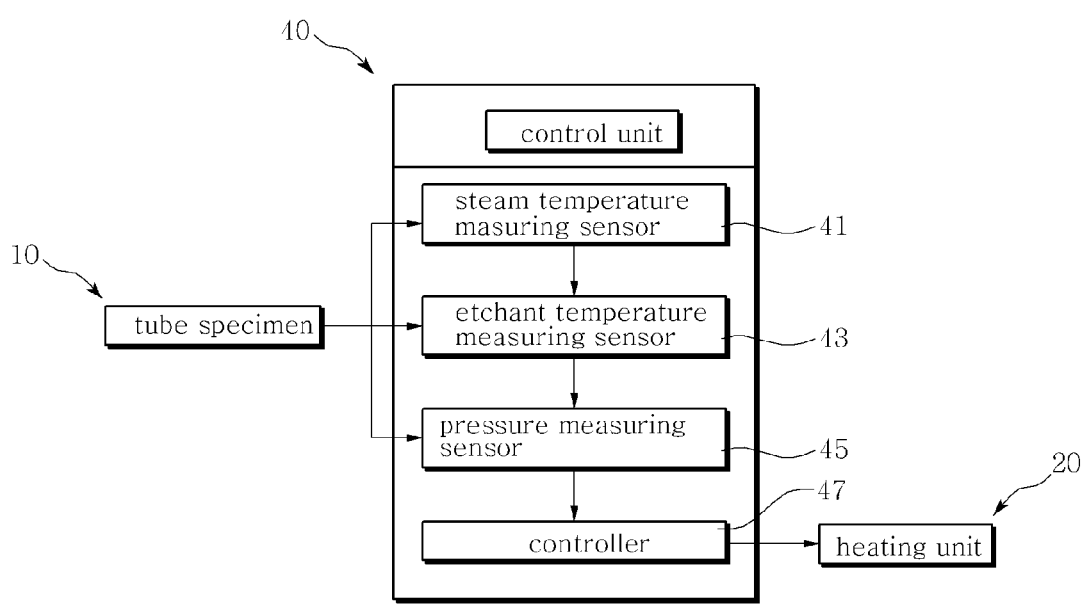
FIG. 6 shows a block diagram of a control unit according to the present invention.

As shown in FIG. 6, the control unit 40 includes a steam temperature measuring sensor 41 provided in the tube specimen 10 to measure the temperature of the steam in the tube specimen 10, an etchant temperature measuring sensor 42 provided in the tube specimen 10 to measure the temperature of an etchant in the tube specimen 10, a pressure measuring sensor 45 for measuring the inner pressure of the tube specimen 10, and a controller 47 such as a micom or a computer electrically connected to the pressure measuring sensor 45 to receive detection signals and to selectively output control signals to the heating unit 20 based on the received detection signals.

The respective sensors and the controller of the control unit 40 are known in the art and thus detailed descriptions thereof are omitted.

Below, an experimental example using the apparatus for forming stress corrosion cracks according to the present invention is described.

EXPERIMENTAL EXAMPLE 1

A specimen for the present experimental example was made of STS 304 (O.D.: 89 mm, t: 7.7 mm, yield strength: 41.8 kg/mm$^2$) useful as a material for nuclear power plant structures.

This specimen had a length l of 500 mm. To control the cracking position in the specimen, a notch having a depth of 0.5 mm was artificially formed at a position in a circumferential direction of the specimen through lathe machining.

In order to set conditions for generation of a stress corrosion crack, 2 mol NaOH and 1 mol $Na_2S$ were placed in the tube specimen 10, and the temperature of 350° C. corresponding to the actual conditions for the generation of a stress corrosion crack in a nuclear power plant was maintained using a heating unit 20 and a control unit 40.

Further, in order to apply at least a yield stress value to the tube specimen 10 at 350° C., a pressure of 170~180 bar was continued. The experimental apparatus was maintained for 450 hours, after which the cracked portion was cut and then observed using an SEM and EDS.

Figure 7:
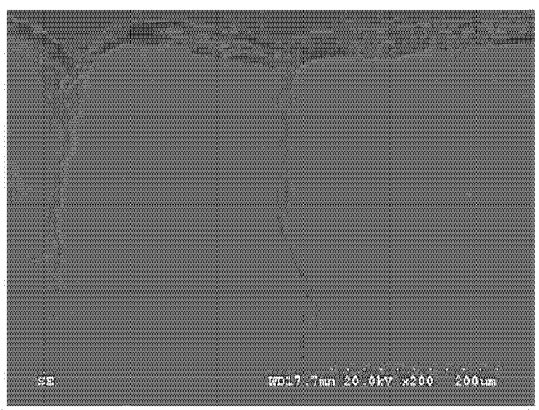
FIG. 7 shows the stress corrosion crack obtained in the example of the present invention, as observed using a scanning electron microscope (SEM)
Figure 7:
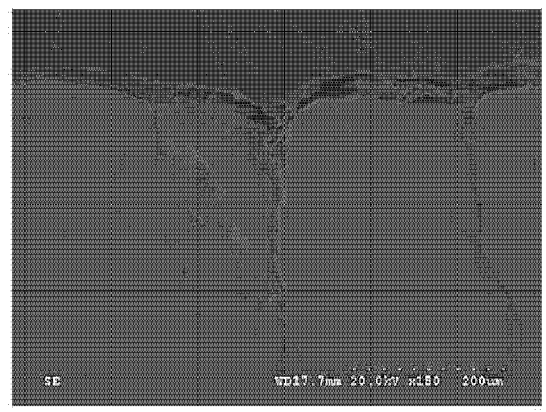
Figure 8:
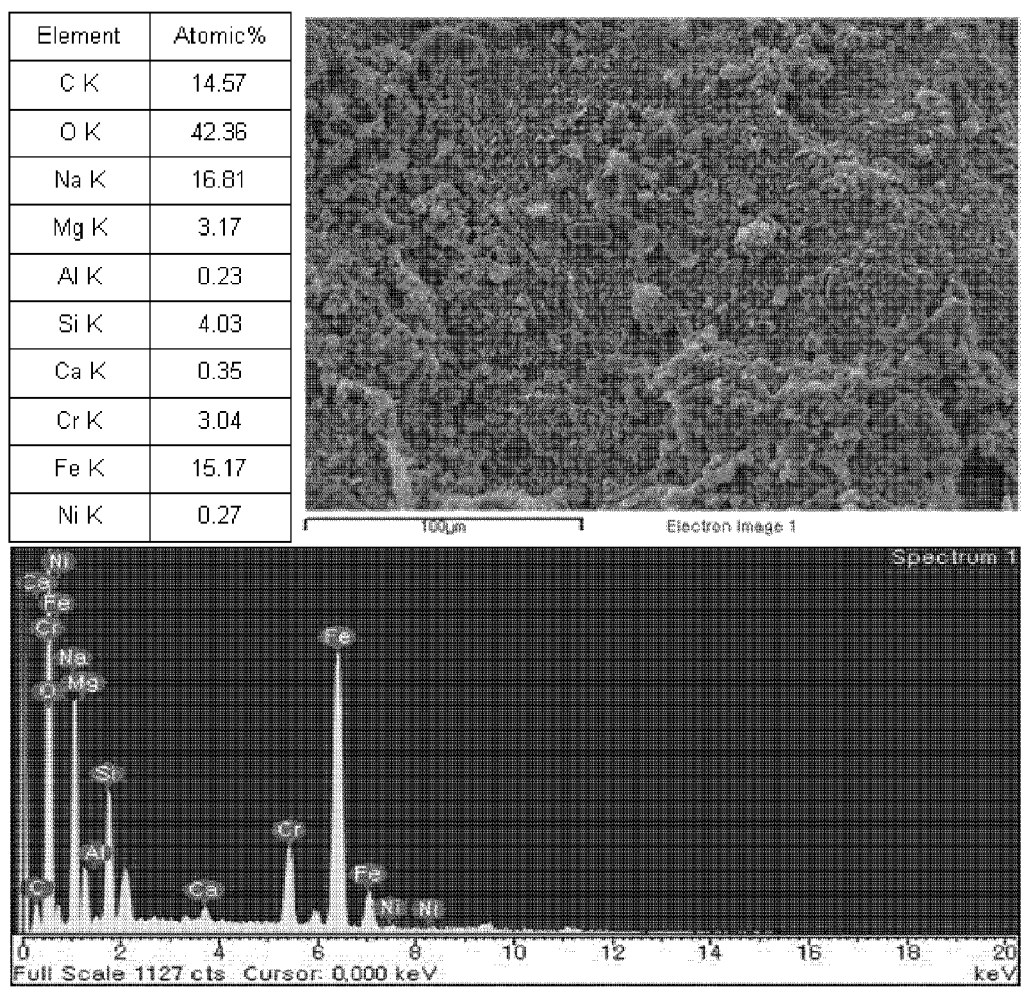
FIG. 8 shows results of analysis of EDS for the upper portion of the tube specimen through which the crack has penetrated.
Figure 9:
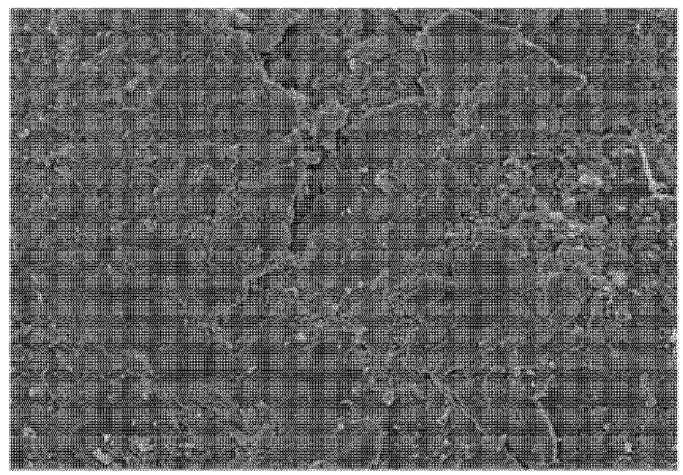
FIG. 9 shows results of analysis of EDS for the lower portion of the tube specimen through which the crack has penetrated.
Figure 9:
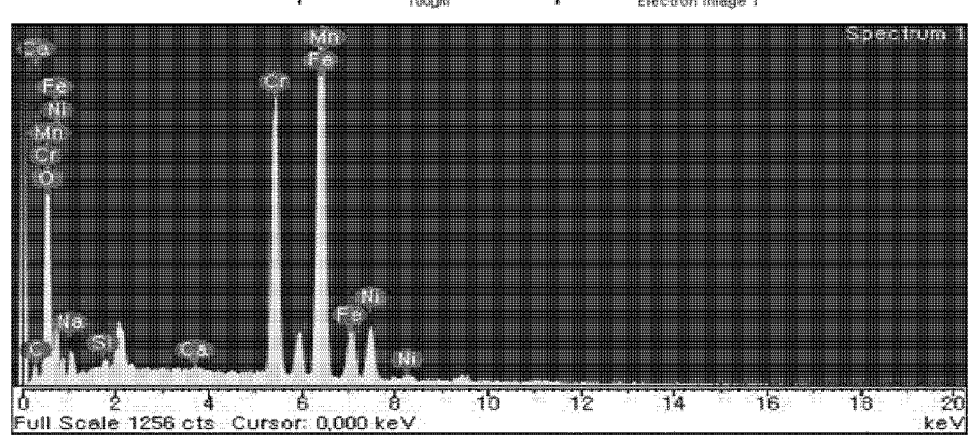

FIG. 7 shows the crack in a longitudinal direction of the tube specimen 10 at the portion of the tube specimen 10 to which stress is intensively applied and with which the etchant is brought into contact, and FIGS. 8 and 9 show EDS and SEM images of the portion of the specimen where the crack is propagated up to the outer surface of the specimen and is thus penetrated therethrough. As is apparent from the results of the analysis of EDS of FIGS. 8 and 9, the atomic % of Na was seen to be decreased toward the lower portion of the specimen from the upper portion thereof. This was considered to be because a crack was first generated at the upper portion of the tube specimen due to the steam generated under stress and corrosion conditions.

As described above, the present invention provides an apparatus for forming a stress corrosion crack. According to the present invention, stress corrosion cracks occurring in the equipment of nuclear power plants or apparatus industries during operation can be formed in a tube specimen under conditions similar to those of the actual environment of nuclear power plants using steam pressure. Thereby, accuracy pertaining to the analysis of properties of stress corrosion cracks which are in actuality generated can be increased, thus improving reliability of nuclear power plants or apparatus industries and effectively assuring nondestructive testing capability, resulting in very useful industrial applicability.

Although the preferred embodiment of the present invention using the tube specimen has been disclosed for illustrative purposes, those skilled in the art will appreciate that various modifications, additions and substitutions are possible, without departing from the scope and spirit of the invention as disclosed in the accompanying claims.

What is claimed is:

1. An apparatus for forming stress corrosion cracks in a tube specimen having two ends, comprising:
    a heating unit, provided on an outer surface of the tube specimen for generating a steam pressure in the tube specimen;
    an end holding unit for closing and sealing both open ends of the tube specimen so that the steam pressure is generated and maintained in the tube specimen, wherein the end holding unit comprises an upper plate and a lower plate for closing both ends of the tube specimen, and a plurality of tension bars disposed around the tube specimen, each of which including a hydraulic or pneumatic cylinder using hydraulic or pneumatic pressure as an operation pressure or an actuator rod using power to adjust a distance between the upper plate and the lower plate;
    a control unit for controlling the heating unit and the end holding unit; and
    a cooling unit connected to the lower plate so that the steam in the tube specimen is passed through the cooling unit having at least a predetermined length for phase transition of steam into water to lower temperature and pressure of the steam.

2. The apparatus as set forth in claim 1, wherein the heating unit comprises a direct heating coil having a heating wire which is heated using power.

3. The apparatus as set forth in claim 1, wherein the control unit comprises a steam temperature measuring sensor for measuring a temperature of the steam in the tube specimen, an etchant temperature measuring sensor for measuring a temperature of an etchant in the tube specimen, a pressure measuring sensor for measuring an inner pressure of the tube specimen, and a controller electrically connected to the pressure measuring sensor to receive detection signals and to selectively output control signals to the heating unit based on the received detection signals.

4. An apparatus for forming stress corrosion cracks in a tube specimen having two ends, comprising:
    a heating unit provided on an outer surface of the tube specimen for generating a steam pressure in the tube specimen;

an end holding unit for closing and sealing both open ends of the tube specimen so that the steam pressure is generated and maintained in the tube specimen, wherein the end holding unit comprises an upper plate and a lower plate for closing both ends of the tube specimen, and a plurality of tension bars disposed around the tube specimen, each of which including a hydraulic or pneumatic cylinder using hydraulic or pneumatic pressure as an operation pressure;

a control unit for controlling the heating unit and the end holding unit; and a cooling unit connected to the lower plate so that the steam in the tube specimen is passed through the cooling unit having at least a predetermined length for phase transition of steam into water to lower temperature and pressure of the steam.

5. The apparatus as set forth in claim 4, wherein the control unit comprises a steam temperature measuring sensor for measuring a temperature of the steam in the tube specimen, an etchant temperature measuring sensor for measuring a temperature of an etchant in the tube specimen, a pressure measuring sensor for measuring an inner pressure of the tube specimen, and a controller electrically connected to the pressure measuring sensor to receive detection signals and to selectively output control signals to the heating unit based on the received detection signals.

* * * * *